(12) United States Patent
Alanzo et al.

(10) Patent No.: US 8,231,886 B2
(45) Date of Patent: Jul. 31, 2012

(54) COSMETIC POWDER COATED WITH ALKOXY SILICONES

(75) Inventors: Vito Alanzo, Castano Primo (IT); Simona Morlacchi, Roncello (IT)

(73) Assignee: Intercos S.p.A., Milan (IT)

( * ) Notice: Subject to any disclaimer, the term of this patent is extended or adjusted under 35 U.S.C. 154(b) by 249 days.

(21) Appl. No.: 12/749,336

(22) Filed: Mar. 29, 2010

(65) Prior Publication Data

US 2010/0255046 A1    Oct. 7, 2010

(30) Foreign Application Priority Data

Apr. 1, 2009    (IT) .................................. MI09A0526

(51) Int. Cl.
| | |
|---|---|
| A61K 8/03 | (2006.01) |
| A61Q 1/12 | (2006.01) |
| A61Q 1/06 | (2006.01) |
| A61Q 1/10 | (2006.01) |

(52) U.S. Cl. ...................................................... 424/401
(58) Field of Classification Search .................. None
See application file for complete search history.

(56) References Cited

U.S. PATENT DOCUMENTS 5,496,544 A    3/1996    Mellul et al.
7,345,131 B2 *    3/2008    Selbertinger et al. ........... 528/34

FOREIGN PATENT DOCUMENTS

| EP | 1116 753 | 7/2001 |
|---|---|---|
| JP | 63165461 | 7/1988 |
| JP | 1182368 | 7/1989 |
| WO | WO 03/043567 | 5/2003 |

OTHER PUBLICATIONS

Database WPI Week 198833, Thomson Scientific, London, GB; AN 1988-231710, XP002563747, Jul. 8, 1988.
Database WPI Week 198935, Thomson Scientific, London, GB; AN 1989-251891, XP002563748, Jul. 20, 1989.
Witucki, Gerald L., "A Silane Primer: Chemistry and Applications of Alkoxy Silanes," Journal of Coatings Technology, vol. 65, No. 822, Jan. 1, 1993, pp. 57-60.

* cited by examiner

*Primary Examiner* — James H Alstrum Acevedo
*Assistant Examiner* — Daniel L Branson
(74) *Attorney, Agent, or Firm* — Novak Druce + Quigg LLP

(57) ABSTRACT

A cosmetic powder, endowed with a hydrophobic coating based on alkoxy silicones, comprising a powder phase and a hydrophobic coating phase, said hydrophobic coating phase completely coats said powder phase and said coating phase consists of a compound of general formula $(RO)_3$—Si—$(CH_2)_3$—NHCOR', where R and R' have the meanings described in the disclosure. A cosmetic composition comprising said powder and to its uses in pressed powder foundations, pressed powder eye shadows, lipsticks or fluid foundations.

10 Claims, No Drawings

COSMETIC POWDER COATED WITH ALKOXY SILICONES

CROSS-REFERENCE TO RELATED APPLICATIONS

This application claims priority to Italian Patent Application MI2009A000526, filed Apr. 1, 2009, the entire contents of which are herein incorporated by reference.

FIELD OF THE INVENTION

The present invention relates to a cosmetic powder endowed with a hydrophobic coating based on alkoxy silicones, preferably for makeup cosmetics, and to a cosmetic composition containing such a coated powder.

BACKGROUND OF THE INVENTION

The cosmetic products, such as foundations, blushers, eye shadows, lipsticks, etc., which are used for the makeup of skin and lips are largely comprised of inorganic powders and various organic powders.

By applying these products on the skin surface, a thin colored film is formed, which serves the function of masking the esthetic skin flaws and conferring a more even appearance.

It is known that direct contact of inorganic and organic cosmetic powders with the skin may lead to the absorption of the water on the skin surface, thus altering the natural hydrophilic and lipophilic balance, which may cause localized dehydration effects and consequently unpleasant feelings by those using these products.

Also, the lack of homogeneity of the powders used, having different physical features from one another, may ultimately generate clearly perceptible defects.

It is known the use of silicones in the field of cosmetic powders.

For example, U.S. Pat. No. 5,496,544 concerns a skin cosmetic composition consisting of an anhydrous powder comprising a solid powder phase mixed with a fat-based binder which contains a silicone mixture comprising at least one silicone oil, at least one silicone wax, at least one silicone resin, and optionally at least on silicone rubber and optionally at least one phenyl dimethicone.

However, in U.S. Pat. No. 5,496,544, the anhydrous powder undergoes a physical treatment by said fat-based binder. Therefore, in the cosmetic composition from U.S. Pat. No. 5,496,544, the absence of a covalent chemical bond between the powder phase and fat-based binder has the drawback of an easy extraction of the latter from the powder phase. Also, in the cosmetic composition from U.S. Pat. No. 5,496,544, the powder phase coating consists of complex mixtures of silicones which confer a different kind of sensorial effects on the skin itself.

EP 1 116 753 describes a powder treated with reactive silicone comprising a powder surface-coated with a silicone compound, in which the amount of hydrogen generated from Si—H groups left on the surface of the silicone-treated powder is not greater than 0.2 ml/g of the treated powder and a contact angle between the water and the treated powder is at least 100°.

However, the direct reaction between methylhydrogenpolysiloxane containing reactive Si—H bonds and the powder surface described in EP 1 116 753 never reaches completion and it has the disadvantage to release some $H_2$ over time, which is the cause of several drawbacks for the obtained cosmetic powder. Indeed, on the one hand the generation of $H_2$ may cause the containers carrying the powder to swell and deteriorate, on the other hand the powder itself may harden and break.

Moreover, the powder obtained by means of the direct reaction between methylhydrogenpolysiloxane containing reactive Si—H bonds and the powder surface itself, once subjected to pressing, exhibits a non-homogeneous and non-compact appearance due to development of $H_2$ over time.

In fact it is known that a cosmetic powder should simultaneously have all the following properties:
- being densely and homogeneously pressed with a drop strength of at least 10 cm,
- being able to give good sensorial feeling features on skin (smoothness or flowingness during application),
- ensuring an excellent skin adhesion so as to be able to last long (long lasting);
- being spreadable and fadeable during application (ease of application)
- being endowed with a good hydrophobicity, i.e. the powder feature of remaining dry in contact with water. Such a feature is commonly measured by determining the surface tension of solutions, with a known surface tension, deposited on the surface of the powder itself.

DETAILED DESCRIPTION OF THE INVENTION

Therefore, the fundamental technical problem of the present invention is to provide a cosmetic powder having all the aforesaid features at the same time.

The Applicant carried out multiple experimental trials before selecting the particular cosmetic powder capable of meeting the aforesaid requirements.

It is therefore a first object of the present invention a cosmetic powder endowed with a hydrophobic coating based on alkoxy silicones, comprising a powder phase and a hydrophobic coating phase, said hydrophobic coating phase completely coats said powder phase and said coating phase consists of a compound of general formula:

(RO)$_3$—Si—(CH$_2$)$_3$—NHCOR' where
R is —CH$_3$ or —CH$_2$CH$_3$; and
R' is a substituent selected from the group consisting of:
a monofunctional hydroxy silicone of formula:

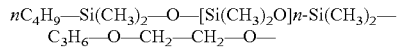
nC$_4$H$_9$—Si(CH$_3$)$_2$—O—[Si(CH$_3$)$_2$O]n-Si(CH$_3$)$_2$—
C$_3$H$_6$—O—CH$_2$—CH$_2$—O— polydimethylsiloxane, α-butyl-ω-[3-(2'-hydroxymethylbutoxy)propyl]-
having a molecular weight between 500 and 10,000 g/mol;
a monofunctional hydroxy silicone of formula:

(CH$_3$)$_3$Si—O—[Si(CH$_3$)$_2$O]n-[CH$_3$SiO(CH$_2$—CH$_2$—CH$_2$—O—)—O]bSi(CH$_3$)$_3$ with b=1, polydimethylsiloxane, γ[3-hydroxypropyl]-
having a molecular weight between 500 and 5000 g/mol; and
a bifunctional hydroxy silicone of formula:

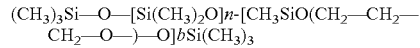
nC$_4$H$_9$—Si(CH$_3$)$_2$—O—[Si(CH$_3$)$_2$O]n-Si(CH$_3$)$_2$—
C$_3$H$_6$—O—CH$_2$—C(CH$_2$—O)$_2$—CH$_2$CH$_3$ polydimethylsiloxane, α-butyl-ω-[3-(2,2-dihydroxymethylbutoxy)propyl]-
having a molecular weight between 1000 and 10,000 g/mol.
Said hydrophobic coating phase advantageously has:
R=—CH$_2$CH$_3$ and
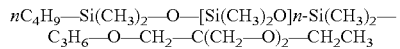
R'=nC$_4$H$_9$—Si(CH$_3$)$_2$—O—[Si(CH$_3$)$_2$O]n—Si(CH$_3$)$_2$—
C$_3$H$_6$—O—CH$_2$—CH$_2$—O— having a molecular weight of 1000 g/mol.

Said hydrophobic coating phase advantageously has:
R=—CH$_2$CH$_3$ and
R'=(CH$_3$)$_3$Si—O—[Si(CH$_3$)$_2$O]n-[CH$_3$Si(CH$_2$—CH$_2$—CH$_2$—O—)—O]bSi(CH$_3$)$_3$
with b=1 having a molecular weight of 740 g/mol.

Said hydrophobic coating phase advantageously has:
R=—CH$_2$CH$_3$ and
R'=nC$_4$H$_9$—Si(CH$_3$)$_2$—O—[Si(CH$_3$)$_2$O]n-Si(CH$_3$)$_2$—C$_3$H$_6$—O—CH$_2$—C(CH$_2$—O)$_2$—CH$_2$CH$_3$—
having a molecular weight of 5000 g/mol.

The hydrophobic coating phase of the cosmetic powder of the present invention is advantageously obtained by the addition reaction of the above-mentioned hydroxy mono and/or bifunctional silicones with a trialkoxy propylisocyanate.

Using the above-mentioned alkoxy silicone as a cosmetic powder coating is novel.

It is therefore a second object of the present invention to use a compound of general formula (RO)$_3$—Si—(CH$_2$)$_3$—NH-COR' in which the substituents R and R' have the above-mentioned meanings, as a hydrophobic coating phase of a cosmetic powder.

The cosmetic powder of the present invention is advantageously used in cosmetic compositions such as pressed powder foundations, pressed powder eye shadows, lipsticks or fluid foundations.

It is then a further object of the present invention a cosmetic composition comprising a cosmetic powder as described above together with other cosmetically acceptable ingredients.

The powder phase of the cosmetic powder of the present invention may consist of organic powders such as, for example, starches and polysaccharides, inorganic powders such as, for example, sericite, mica, talc, silica, iron oxides, zinc oxides, titanium oxides, boron nitride and pearls (mica-titanium dioxide).

Said powder phase preferably consists of inorganic powders, still more preferably it consists of talc.

The cosmetic composition of the present invention may contain other well-known ingredients used in the cosmetic field such as, for example, powdered polymers, oils and fats, silicones, perfluorinated compounds, fragrances and flavors, dyes and pigments.

The process for preparing the hydrophobic coating phase according to the present invention is as follows:

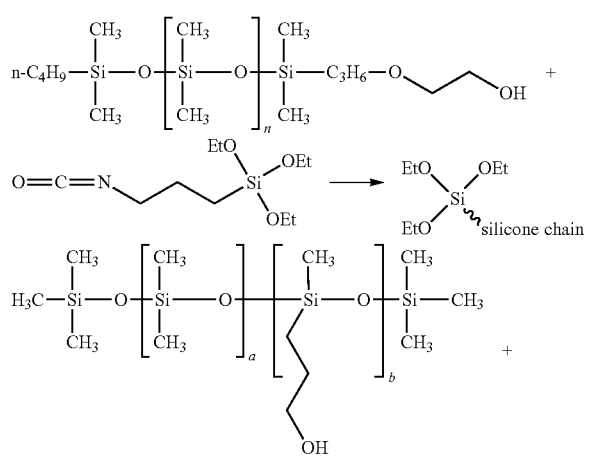

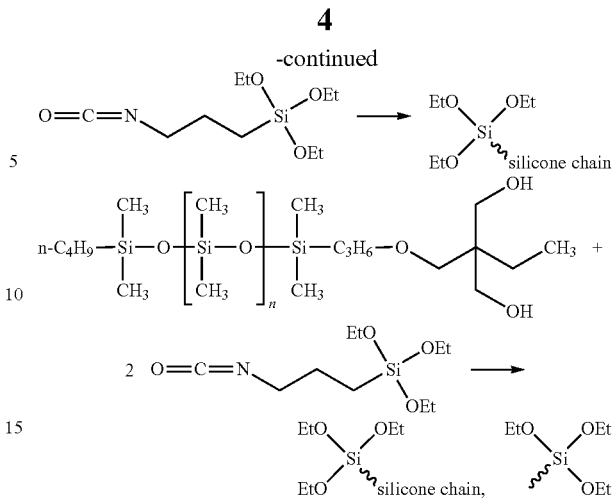

The aforesaid hydrophobic coating phase of the present invention is prepared by mixing hydroxy silicone and isocyanate and heating the mixture at a temperature of 95° C. for about 12 hr until complete disappearance of the existing isocyanate groups.

The whole preparation process is carried out under a nitrogen flux so as to have a totally inert environment within the mixer.

Hydroxy silicone and isocyanate used to obtain the coating phase of the present invention are advantageously readily available on the market.

In fact mono and/or bifunctional hydroxy silicones may be supplied from CHISSO Corporation, Inc., Tokyo (Japan) or Siltech-LLC, Georgia (USA), while isocyanate propyltriethoxysilane may be supplied from GE Advanced Material—North America, Wilton (USA).

Once the coating phase of the present invention has been obtained as described above, the cosmetic powder of the present invention is prepared by atomizing said hydrophobic coating phase in the form of a solution on the powder phase under stirring. Once the atomization has been accomplished, the obtained product is transferred to an oven at a temperature of about 80° C. where it remains until complete solvent evaporation and, finally, the obtained powder may be sieved upon cooling the same at room temperature.

Advantageously, for the atomization, the hydrophobic coating phase of the present invention is in the form of an alcoholic solution, even more advantageously it is an isopropyl alcohol solution.

The chemical and especially physical features of the hydrophobic coating of the present invention are such to allow to completely coat the powder phase thus creating a thin layer (film) with physical properties which resemble the coating properties, i.e. flexibility, elasticity and softness of the film, which does not break.

The Applicant experienced that the cosmetic powder coating obtained by using other silicone polymers, having a different chemical nature as compared to that of the present invention, and above all different physical features such as, for example trimethylsiloxysilicate, leads to deposition of a layer which is rigid, crystalline and much less flexible thus conferring unpleasant sensorial properties, such as a dry skin feeling, to the products containing it.

On the other hand, cosmetic benefits obtained by the cosmetic powder of the present invention result from sensorial tests conducted on a group of volunteer panelists, which focused on the evaluation of the cosmetic properties. The result of these tests is shown in the experimental part described hereinafter.

EXAMPLES

The following examples are intended to illustrate the present invention, but not to limit it in any way.

Example 1

Preparation of the Hydrophobic Coating Phase of the Invention with a Monofunctional Hydroxy Silicone of the Present Invention

|  | Compound | % (w/w) |
|---|---|---|
| Phase A | 3-(triethoxysilyl)propylisocyanate, 95% | 24.719 |
|  | polydimethylsiloxane,γ[3-hydroxypropyl]- MW = 740 g/mol | 74.231 |
|  | zinc stearate | 0.050 |
| Phase B | isopropyl alcohol | 1.000 |

The aforesaid hydrophobic coating phase was prepared by loading phase A into a reactor provided with stirrer, thermometer and condenser under nitrogen and heating the mass at a temperature of 95° C. for about 12 hr until complete disappearance of the existing isocyanate groups. The aforesaid disappearance was evaluated by IR.

The product so obtained showed the following physical-chemical features: clear, viscous liquid. Such a product was cooled and then diluted with phase B. A clear solution having a viscosity of 230 MPasec (25° C.) and a dry content at 105° C. of 99% was obtained.

Example 2

Preparation of the Hydrophobic Coating Phase of the Invention with a Bifunctional Hydroxy Silicone of the Present Invention

| Compound | % (w/w) |
|---|---|
| 3-(triethoxysilyl)propylisocyanate, 95% | 32.029 |
| polydimethylsiloxane,α-butyl-ω-[3-(2,2-dihydroxymethylbutoxy)propyl]- MW = 1000 g/mol | 67.971 |

The aforesaid hydrophobic coating phase was prepared by loading the constituents into a reactor provided with stirrer, thermometer and condenser under nitrogen and heating the mass at a temperature of 95° C. for about 12 hr until complete disappearance of the existing isocyanate groups. The aforesaid disappearance was evaluated by IR. The product so obtained showed the following physical-chemical features: clear, viscous liquid. Such a product was cooled and then diluted with phase B. A clear solution having a viscosity of 330 MPasec (25° C.) was obtained.

Example 3

Preparation of the Hydrophobic Coating Phase of the Invention with a Monofunctional Hydroxy Silicone of the Present Invention

|  | Compound | % (w/w) |
|---|---|---|
| Phase A | 3-(triethoxysilyl)propylisocyanate, 95% | 2.377 |
|  | polydimethylsiloxane,α-butyl-ω-[3-(2,2-dihydroxymethylbutoxy)propyl]- MW = 10,000 g/mol | 96.573 |
|  | zinc stearate | 0.050 |
| Phase B | isopropyl alcohol | 1.000 |

The aforesaid hydrophobic coating phase was prepared as described in the Example 1. Before diluting with isopropyl alcohol, the obtained product showed the following physical-chemical features: clear, viscous liquid. Such a product was cooled and then diluted with phase B. A clear solution having a viscosity of 350 MPasec (25° C.) and a dry content at 105° C. of 99% was obtained.

Example 4

Preparation of the Hydrophobic Coating Phase of the Invention with a Monofunctional Hydroxy Silicone of the Present Invention

|  | Compound | % (w/w) |
|---|---|---|
| Phase A | 3-(triethoxysilyl)propylisocyanate, 95% | 17.512 |
|  | polydimethylsiloxane,α-butyl-ω-[3-(2,2-dihydroxymethylbutoxy)propyl]- MW = 1000 g/mol | 81.438 |
|  | zinc stearate | 0.050 |
| Phase B | isopropyl alcohol | 1.000 |

The aforesaid hydrophobic coating phase was prepared as described in the Example 1. Before diluting with isopropyl alcohol, the obtained product showed the following physical-chemical features: clear, viscous liquid. Such a product was cooled and then diluted with phase B. A clear solution having a viscosity of 175 MPasec (25° C.) and a dry content at 105° C. of 99% was obtained.

Example 5

Preparation of the Hydrophobic Coating Phase of the Invention with a Monofunctional Hydroxy Silicone of the Present Invention

|  | Compound | % (w/w) |
|---|---|---|
| Phase A | 3-(triethoxysilyl)propylisocyanate, 95% | 4.655 |
|  | poliydimethylsiloxane,α-butyl-ω-[3-(2,2-dihydroxymethylbutoxy)propyl]- | 94.295 |

-continued

|       | Compound                              | % (w/w) |
|-------|---------------------------------------|---------|
|       | MW = 5000 g/mol<br>zinc stearate      | 0.050   |
| Phase B | isopropyl alcohol                   | 1.000   |

The aforesaid hydrophobic coating phase was prepared as described in the Example 1. Before diluting with isopropyl alcohol, the obtained product showed the following physical-chemical features: clear, viscous liquid. Such a product was cooled and then diluted with phase B. A clear solution having a viscosity of 230 MPasec (25° C.) and a dry content at 105° C. of 90% was obtained.

Example 6

Preparation of a Cosmetic Powder of the Invention

|         | Compound                              | % (w/w) |
|---------|---------------------------------------|---------|
| Phase A | Talc                                  | 91.10   |
| Phase B | coating of the Example 1 (REM 553.11) | 4.55    |
|         | deionized water                       | 4.15    |
|         | guanidine carbonate 99%               | 0.20    |

The aforesaid cosmetic powder was prepared by loading phase A into a mill having a helical mixer equipped with melting apparatus, atomization pump and tubing insulated by cooling water opened by blending for about 2 min and, when blending, phase B was atomized until the depletion of the liquid. The whole was then allowed to ripen at room temperature for about 24 hr. The powder so obtained was dried into an oven at about 80° C. and the volatile products were controlled to be <1%. Finally, the powder was sieved on a 90 mesh sieving screen. The powder pressed in a metal wafer has a surface tension value of 33 dyne/cm.

Example 7

Preparation of a Cosmetic Powder of the Invention

|         | Compound                              | % (w/w) |
|---------|---------------------------------------|---------|
| Phase A | Talc                                  | 83.229  |
| Phase B | coating of the Example 2 (REM 553.11) | 4.162   |
|         | ethyl alcohol; 96% pure               | 8.323   |
| Phase C | deionized water                       | 4.162   |
|         | guanidine carbonate 99%               | 0.125   |

The aforesaid cosmetic powder was prepared by loading phase A into a mill having a helical mixer equipped with a melting apparatus, atomization pump and insulated tubing with cooling water opened by blending for about 2 min and, when blending, phase B and then phase C were atomized until the depletion of the liquid. The whole was then allowed to ripen at room temperature for about 24 hr. The powder so obtained was dried into an oven at about 80° C. and the volatile products were controlled to be <1%. Finally, the powder was sieved on a 90 mesh sieving screen. The powder pressed in a metal wafer had a surface tension value of 33 dyne/cm.

Example 8

Preparation of a Cosmetic Powder of the Invention

|         | Compound                              | % (w/w) |
|---------|---------------------------------------|---------|
| Phase A | talc                                  | 91.10   |
| Phase B | coating of the Example 3 (REM 553.11) | 4.55    |
| Phase C | deionized water                       | 4.15    |
|         | guanidine carbonate 99%               | 0.20    |

The aforesaid cosmetic powder was prepared as described in the Example 7. The powder pressed in a metal wafer had a surface tension value of 33 dyne/cm.

Example 9

Preparation of a Cosmetic Powder of the Invention

|         | Compound                              | % (w/w) |
|---------|---------------------------------------|---------|
| Phase A | talc                                  | 91.10   |
| Phase B | coating of the Example 4 (REM 553.11) | 4.55    |
| Phase C | deionized water                       | 4.15    |
|         | guanidine carbonate 99%               | 0.20    |

The aforesaid cosmetic powder was prepared as described in the Example 7. The powder pressed in a metal wafer had a surface tension value of 33 dyne/cm.

Example 10

Preparation of a Cosmetic Powder of the Invention

|         | Compound                              | % (w/w) |
|---------|---------------------------------------|---------|
| Phase A | Talc                                  | 91.10   |
| Phase B | Coating of the Example 5 (REM 553.11) | 4.55    |
| Phase C | deionized water                       | 4.15    |
|         | guanidine carbonate 99%               | 0.20    |

The aforesaid cosmetic powder was prepared as described in the Example 7. The powder pressed in a metal wafer had a surface tension value of 33 dyne/cm.

Example 11

Preparation of a Cosmetic Composition of the Invention in the Form of a Pressed Powder Foundation

| Compound                                          | % weight |
|---------------------------------------------------|----------|
| Talc coated with the coating phase of the Example 4 | 75.02    |
| Mica coated with the coating phase of the Example 4 | 5.25     |

-continued

| Compound | % weight |
|---|---|
| Yellow iron oxide coated with the coating phase of the Example 4 | 1.50 |
| Red iron oxide coated with the coating phase of the Example 4 | 0.62 |
| Black iron oxide coated with the coating phase of the Example 4 | 0.25 |
| Brown iron oxide coated with the coating phase of the Example 4 | 0.56 |
| Spherical silica coated with the coating phase of the Example 4 | 9.50 |
| Titanium dioxide coated with the coating phase of the Example 4 | 1.00 |
| Nylon-12 | 3.00 |
| Octyldodecylstearoylstearate | 3.00 |
| Preservatives | 0.30 |
| TOTAL | 100.00 |

Example 12

Preparation of a Cosmetic Composition of the Invention in the Form of a Pressed Powder Eye Shadow

| Compound | % weight |
|---|---|
| Talc coated with the coating phase of the Example 4 | 59.00 |
| Mica coated with the coating phase of the Example 4 | 4.00 |
| Yellow iron oxide coated with the coating phase of the Example 4 | 6.50 |
| Red iron oxide coated with the coating phase of the Example 4 | 3.00 |
| Black iron oxide coated with the coating phase of the Example 4 | 0.20 |
| Spherical silica coated with the coating phase of the Example 4 | 2.00 |
| Pearls (Titanium - Mica) coated with the coating phase of the Example 4 | 6.80 |
| Pearls (iron-titanium oxides) coated with the coating phase of the Example 4 | 12.20 |
| Octyldodecylstearoylstearate | 3.00 |
| Cetearyloctanoate | 3.00 |
| Preservatives | 0.30 |
| TOTAL | 100.00 |

Example 13

Preparation of a Cosmetic Composition of the Invention in the Form of a Lipstick

| Compound | % weight |
|---|---|
| Fat phase for lipsticks | 88.0 |
| Red iron oxide coated with the coating phase of the Example 4 | 2.70 |
| Lacquer FD&C Red 7 Al coated with the coating phase of the Example 4 | 0.55 |
| FD&C Yellow 5 coated with the coating phase of the Example 4 | 1.30 |
| Pearls (mica-titanium dioxide) coated with the coating phase of the Example 4 | 6.25 |
| Titanium dioxide coated with the coating phase of the Example 4 | 1.20 |
| TOTAL | 100.00 |

Example 14

Preparation of a Cosmetic Composition of the Invention in the Form of a Fluid Foundation

| Compound | % weight |
|---|---|
| Microcrystalline wax | 1.40 |
| Laureth-9 | 0.60 |
| Polyglyceryl-4 isostearate | 0.80 |
| Cyclomethicone | 13.90 |
| Silicone derivatives | 20.50 |
| Propylene glycol | 4.00 |
| Glycerin | 2.00 |
| Sodium chloride | 1.60 |
| Preservatives | 0.30 |
| Water | 40.70 |
| Red iron oxide coated with the coating phase of the Example 4 | 1.40 |
| Black iron oxide coated with the coating phase of the Example 4 | 0.20 |
| Yellow iron oxide coated with the coating phase of the Example 4 | 3.20 |
| Titanium dioxide coated with the coating phase of the Example 4 | 8.20 |
| Talc coated with the coating phase of the Example 4 | 1.20 |
| TOTAL | 100.00 |

Sensorial Tests

The properties of the cosmetic powder of the present invention were evaluated by means of sensorial tests conducted on voluntary panelists.

The assayed features of the powders of the present invention (Examples 6, 7, 8, 9 and 10 illustrated above) were as follows.

a) Mechanical property of the pressed powder

Drop strength: the test consists in evaluating the cohesive property of the powder pressed in a metal wafer when it is dropped from a height of 20 cm.

b) Cosmetic (sensorial) properties of the pressed powders

Smoothness or flowingness during application: consisting in the (sensorial) evaluation of the aforesaid feature during the application step.

Spreadability and fadeability of the powder: the test consists in evaluating the ease of collecting the cosmetic powder and the capacity of deposition thereof on the skin surface.

Adhesion: the test consists in evaluating the ability of the powder to attach to and remain on the skin surface.

Long lasting: the test consists in evaluating the ability of the powder to remain on the skin for 6 hr.

Homogeneity: the test consists in evaluating the uniformity of the powder layer on the skin upon application.

During the aforesaid assays, for each product under examination, the panelists indicated whether the tested compositions gave an average result (0), a poor result (−), a good result (+) and an excellent result (++), regarding the investigated properties.

The results for the powders of the present invention are shown in the following Table 1.

TABLE 1

| Cosmetic property | Ex. 6 | Ex. 7 | Ex. 8 | Ex. 9 | Ex. 10 |
|---|---|---|---|---|---|
| Drop strength | ++ | ++ | ++ | ++ | ++ |
| Smoothness during application | ++ | + | + | ++ | ++ |
| Spreadability and fadeability | ++ | ++ | ++ | ++ | ++ |
| Adhesion | ++ | + | + | ++ | ++ |
| Long lasting | + | + | + | + | + |
| Homogeneity | ++ | + | + | ++ | ++ |

Comparative Examples

Sensorial Tests

As set forth above, the properties of cosmetic powders coated with silicone polymers having a chemical nature different from that of the present invention were assayed.

The aforesaid cosmetic powders differed from those of the present invention solely regarding the coating type, while amounts and type of other ingredients remained the same.

In fact, similarly to the powders of the present invention, the comparative powders had a phase A consisting of talc (91.10% w/w), and a phase C consisting of deionized water (4.15% w/w) and guanidine carbonate 99% (0.20% w/w).

Regarding the coating phase B (4.55% w/w), instead, the powder of the comparative Example 1 was formed by cetyl dimethycone, beenoxy dimethycone, trimethylsiloxysilicate polydimethyl siloxane having a low viscosity (U.S. Pat. No. 5,496,544, Example 2, Part B).

Regarding the coating phase B (4.55% w/w), instead, the powder of the comparative Example 2 was formed by methylhydrogenpolysiloxane (EP 1 116 753, Example 1, Silicone KF99 from Shin-Etsu Chemical).

Regarding the coating phase B (4.55% w/w), instead, the powder of the comparative Example 3 was formed by trimethylsiloxysilicate in dimethycone (DOW CORNING® DC 593).

The Results for the comparative powders are shown in the following Table 2.

TABLE 2

| Cosmetic property | Comp Ex. 1 | Comp Ex. 2 | Comp Ex. 3 |
|---|---|---|---|
| Drop strength | + | + | − |
| Smoothness during application | + | + | − |
| Spreadability and fadeability | 0 | + | − |
| Adhesion | + | + | + |
| Long lasting | 0 | + | + |
| Homogeneity | + | + | 0 |

The invention claimed is:

1. A cosmetic powder, endowed with an hydrophobic coating based on alkoxy silicones, comprising a powder phase and an hydrophobic coating phase, said hydrophobic coating phase wholly coats said powder phase and said coating phase is constituted by a compound of general formula:

$(RO)_3$—Si—$(CH_2)_3$—NHCOR' wherein

R is —$CH_3$ or —$CH_2CH_3$; and

R' is a substituent selected from the group consisting of:
monofunctional hydroxy silicone of formula:

$nC_4H_9$—Si$(CH_3)_2$—O—[Si$(CH_3)_2$O]$n$-Si$(CH_3)_2$—
$C_3H_6$—O—$CH_2$—$CH_2$—O— polydimethylsiloxane,α-butyl-ω[3-(2'-hydroxyethoxy)propyl]-
having a molecular weight between 500 and 10,000 g/mol;
monofunctional hydroxy silicone of formula:

$(CH_3)_3$Si—O—[Si$(CH_3)_2$O]$n$-[$CH_3$Si$(CH_2$—$CH_2$—O—)—O]$b$-Si$(CH_3)_3$ with b=1, polydimethylsiloxane,γ[3-hydroxypropyl]-
having a molecular weight between 500 and 5000 g/mol; and
bifunctional hydroxy silicone of formula:

$nC_4H_9$—Si$(CH_3)_2$—O—[Si$(CH_3)_2$O]$n$-Si$(CH_3)_2$—
$C_3H_6$—O—$CH_2$—C$(CH_2$O—)$CH_2CH_3$ polydimethylsiloxane,α-butyl-ω-[3-(2,2-dihydroxymethylbutoxy)propyl]-
having a molecular weight between 1000 and 10,000 g/mol.

2. Cosmetic powder according to claim 1, wherein said hydrophobic coating phase has:

R=—$CH_2CH_3$ and
R'=$nC_4H_9$—Si—O—$(CH_3)_2$—[Si$(CH_3)_2$O]n-Si$(CH_3)_2$—$C_3H_6$—O—$CH_2$—$CH_2$—O— having a molecular weight of 1000 g/mol.

3. Cosmetic powder according to claim 1, wherein said hydrophobic coating phase has:

R=—$CH_2CH_3$ and
R'=$(CH_3)_3$Si—O—[Si$(CH_3)_2$O]n-[$CH_3$Si$(CH_2$—$CH_2$—$CH_2$—O—)—O-]$b$Si$(CH_3)_3$
with b=1 having a molecular weight of 740 g/mol.

4. Cosmetic powder according to claim 1, wherein said hydrophobic coating phase has:

R=—$CH_2CH_3$ and
R'=$nC_4H_9$—Si$(CH_3)_2$—O—[Si$(CH_3)_2$O]n-OSi$(CH_3)_2$—$C_3H_6$—O—$CH_2$—C$(CH_2$—O—)$_2$—$CH_2CH_3$
having a molecular weight of 5000 g/mol.

5. A method of improving the appearance of skin, comprising: applying a cosmetic powder according to claim 1 to skin of a user.

6. The method according to claim 5, wherein said cosmetic powder is in the form of a pressed powder foundation.

7. The method according to claim 5, wherein said cosmetic powder is in the form of a pressed powder eyeshadow.

8. The method according to claim 5, wherein said cosmetic powder is in the form of a lipstick.

9. The method according to claim 5, wherein said cosmetic powder is in the form of a fluid foundation.

10. A cosmetic composition comprising:
a cosmetic powder according to claim 1; and
a cosmetically acceptable excipient.

* * * * *